United States Patent [19]

Takahashi et al.

[11] Patent Number: 4,968,305

[45] Date of Patent: Nov. 6, 1990

[54] RADIATION-SHIELDING INJECTOR FOR A RADIO-PHARMACEUTICAL LIQUID COMPOSITION

[75] Inventors: Jun Takahashi, Ichihara; Shinsuke Tanaka, Chiba; Mitsuhisa Iinuma, Nagoya; Nobuo Ueda, Chiba, all of Japan

[73] Assignee: Nihon Medi-Physics Co., Ltd., Takarazuka, Japan

[21] Appl. No.: 166,982

[22] Filed: Mar. 11, 1988

[30] Foreign Application Priority Data

Mar. 11, 1987 [JP] Japan .............................. 62-35558[U]

[51] Int. Cl.$^5$ ................................................ A61M 245
[52] U.S. Cl. .................................................... 604/232
[58] Field of Search ............................. 604/232–235, 604/187, 227, 225

[56] References Cited

U.S. PATENT DOCUMENTS

| Re. 16,836 | 12/1927 | Cook | 604/241 |
|---|---|---|---|
| 679,198 | 7/1901 | Witkowski | 604/232 |
| 1,328,203 | 1/1920 | Riethmüller | 604/227 |
| 2,737,949 | 3/1956 | Brown | 604/192 |
| 2,813,528 | 11/1957 | Blackman | 604/232 |
| 3,110,309 | 11/1963 | Higgins | 604/232 |
| 3,158,155 | 11/1964 | Myerson et al. | 604/232 |
| 3,220,412 | 11/1965 | McConnaughey et al. | 604/235 |
| 3,811,441 | 5/1974 | Sarnoff | 604/232 |

FOREIGN PATENT DOCUMENTS 0515066  7/1954  Belgium .............................. 604/233

*Primary Examiner*—C. Fred Rosenbaum
*Assistant Examiner*—Sharon Rose
*Attorney, Agent, or Firm*—Jones, Tullar & Cooper

[57] ABSTRACT

A kit for the administration of a radiopharmaceutical liquid composition has been developed, which includes a radiation-shielding injector accompanied with a syringe-type vial having a gasket therein, a seal cap and a plunger to be engaged with the gasket. The injector is made of a radiation-shielding tubular metal body covered with a plastic material having an exit at the bottom, the body being further provided with a lead glass window on its curved surface, a packing engaging the inside surface at one end of the body and a pair of wings having skid-proof ridges formed on at least one surface thereof, the wings being located at one end of the body. The body is so designed as to be shorter than the tubular portion of the syringe-type vial to be inserted therein, whereby the rear portion of the vial protrudes a little from the tubular body when the same is inserted into the body.

2 Claims, 1 Drawing Sheet

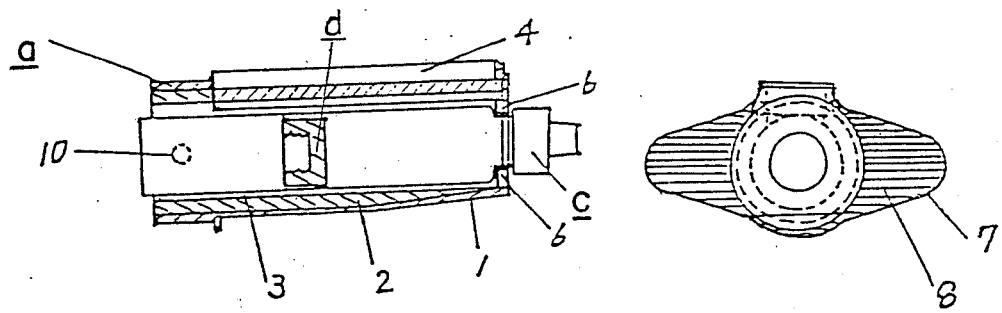
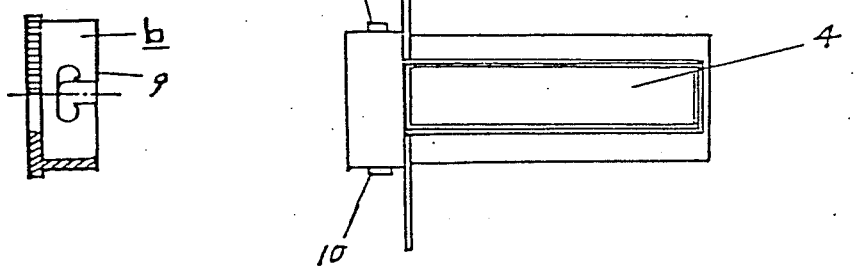
Fig. 4 Fig. 3
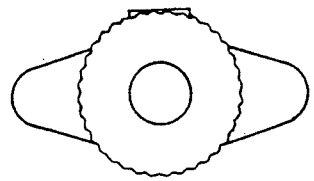
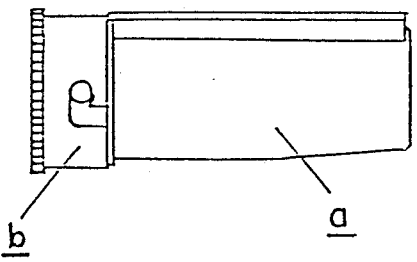
Fig. 6 Fig. 5
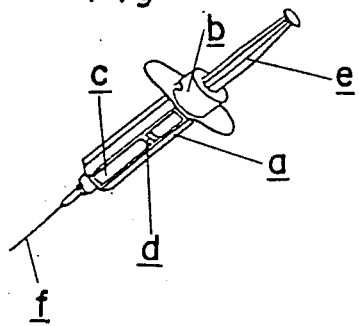
Fig. 7

RADIATION-SHIELDING INJECTOR FOR A RADIO-PHARMACEUTICAL LIQUID COMPOSITION

BACKGROUND OF THE INVENTION

1. Field of the Invention

This invention relates to a radiation-shielding injector for a radiopharmaceutical liquid composition. More particularly, it relates to a radiation-shielding injector accompanied with a syringe-type vial filled with a radiopharmaceutical liquid composition, which is so designed as to prevent the fingers or the body of an operator from radiation exposure on administration.

2. Prior Art

Conventionally, the radiopharmaceutical liquid composition is contained in a glass vial and tightly sealed with a rubber septum. On practical applications at diagnostic or therapeutic institutions, such as hospitals, the radiopharmaceutical liquid composition is once transferred to a disposable syringe and administered to the patient, so that the radiation exposure of the operator becomes a serious problem. Recently, with a high demand for preventing the operator from radiation exposure on transference, there has been proposed a syringe-type container filled with a radiopharmaceutical liquid composition, which is usable as a kit in association with additional assemblies such as a needle and a plunger, whereby no transference of the radiopharmaceutical liquid composition becomes necessary.

The commercially available syringe-type containers comprise in general three assemblies, i.e. an outer lead cylinder, a middle plastic cylinder and an inner syringe-type glass vial or container inserted thereinto. Due to such a construction, the entire size of the container inevitably becomes so large that the administration is cumbersome and inconvenient. Further, the conventional containers have the disadvantage that a firm attachment of the middle plastic cylinder as well as the inner syringe-type glass vial or container to the outer lead cylinder can not be stably performed and a large part of the assembly is contaminated with radioactive material, thereby causing a serious social problem in disposal of a large number of radioactive wastes.

SUMMARY OF THE INVENTION

In order to overcome these drawbacks as seen in the conventional injectors, an object of the invention is to provide an improved radiation-shielding injector accompanied with a syringe-type vial for preventing the operator from radiation exposure or reducing the extent of exposure dose at the time of administration of the radiopharmaceutical liquid composition. Namely, the injector of the invention is so designed as to minimize the overall size of the injector as much as possible and make the attachment of the syringe-type vial stable onto the outer injector. With these improvements, it has now become possible for the operator to expose himself to radiation to a lesser degree and to make handling of the injector on administration more convenient. Further, the disposal of the radioactive wastes is greatly reduced.

According to the preferred embodiment of the invention, there is provided a kit for administration of a radiopharmaceutical liquid composition. The kit comprises a radiation-shielding injector accompanied with a syringe-type vial having a gasket therein, a seal cap and a plunger to be engaged with the gasket. The injector is made of a radiation-shielding tubular metal body (e.g. lead) covered with a plastic material having an exit at the bottom, the tubular body being further provided with a lead glass window on the curved surface, a packing at an inside bottom and a pair of wings having skid-proof ridges on its back around the entrance periphery of the body and being so designed as to be shorter than the tubular portion of the syringe-type vial to be inserted therein, whereby the rear portion of the vial protrudes a little from the tubular body when the same is inserted into the body.

BRIEF DESCRIPTION OF THE DRAWINGS

The present invention will be illustrated in conjunction with the accompanying drawings wherein:

FIG. 1 is a sectional view of the tubular body a into which the syringe-type vial c is inserted;

FIGS. 2 and 3 are respectively a right side view and a plan view of the tubular body a;

FIG. 4 is a partial cross sectional front view of the seal cap b;

FIGS. 5 and 6 are respectively a front view and a left side view of an assembly comprising the tubular body a and the seal cap b;

FIG. 7 is a perspective view of a kit comprising a tubular body a, a seal cap b, a syringe-type vial c, a plunger e engaged in a gasket d in the vial and a needle f, assembled on administration.

DETAILED DESCRIPTION OF A PREFERRED EMBODIMENT

Referring to the drawings, a preferred embodiment of the invention is described further in detail. Namely, in FIGS. 1, 2 and 3, the injector of the invention comprises the tubular body a made of a lead tube 2 covered with the plastic material 1 having an exit at the bottom. The inside of the body a forms a cavity 3 which receives a syringe-type vial c. At the curved surface of the body a, there is provided a lead glass window 4, through which the proper dosing of the liquid composition is ascertained. The body a is further provided with a packing 6 at the inside bottom, a pair of wings 7 having skid-proof ridges 8 on its back as a finger-grip positioned around the entrance periphery of the body a and a pair of protrusions 10 on the curved surface between the entrance edge and the wings 7 for firm attachment of a seal cap b to the body a. In FIG. 2, there is shown skip-proof ridges 8 on the back of the wings 7 to assure a stable handling of the injector in practical use. FIG. 4 shows a pair of hook-shaped slits 9 on the curved surface of the seal cap b, which is to be engaged with the protrusions 10 (FIG. 5) on the body a for their firm attachment. On administration of a radiopharmaceutical liquid composition, the plastic plunger e is inserted into a gasket d accommodated in the syringe-type vial c and a needle f is provided on the top portion of the vial c protruded through the exit of the body a as shown in FIG. 7.

More specifically, the axial length of the body a is so designed as to be slightly shorter than that of the tubular portion of the syringe-type vial c. Accordingly, when the vial c is inserted into the cavity 3 of the body a, the rear portion thereof protrudes a little from the cavity 3, so that only the seal cap b has a possibility to be contaminated with radioactive material, whereby the radioactive wastes such as contaminated parts of the injector is reduced. Namely, by the use of a disposable seal cap b, the radioactive waste can be reduced as much as possible. Furthermore, since the body a is hardly contaminated with radioactive material as mentioned above, there is no need to insert a plastic cylinder for contamination-proof into the cavity 3 as conventionally adopted. This makes it possible to minimize the size of the body a. Moreover, with the provision of the skid-proof ridges 8 at the back of the wings 7, the injector according to the invention can be held more firmly by the hand of an operator and easily handled on injection.

Still, in the embodiment of the invention, the firm attachment of the seal cap b to the body a is made by the engagement of the pair of protrusions 10 provided on the curved surface of the body a with the hook-shaped slits 9 on the curved surface on the seal cap b, as illustrated in FIG. 4 of the drawing. However, other attaching methods using a screw, etc. may be also employable to accomplish the same object of the invention.

What is claimed is:

1. A radiation-shielding injector kit for the administration of radio-pharmaceutical liquid, which comprises:
    a tubular radiation-shielding metallic body covered with a plastic material, said body being open at one end and closed at its other end, with the closed end having a through-hole therethrough, said body having a see-through lead glass window on its curved surface and a pair of wings extending from the body in the vicinity of its open end, said pair of wings having skid-proof ridges on each surface thereof;
    a syringe-type vial pre-filled with a radiopharmaceutical liquid and having a gasket therein, said vial being received within said body, said vial having a slightly longer length than the length of said body;
    a packing situated in the through-hole of the closed end through which said vial passes to contact with an inner surface of the through-hole to be fixed to said body;
    a seal end cap detachably coupled to said body at its open end and having a through-hole, said seal end cap pressing said vial toward said packing so that said vial is fixed to said body; and
    a plunger which passes through the through-hole of the seal end cap and engages the gasket;
    wherein said tubular body has a slightly shorter length than the length of said vial such that said vial is fixed, in its longitudinal direction, between the closed end of said body and said seal end cap.

2. The kit according to claim 1, wherein said body further has protrusions at its open end for fastening said seal end cap to said body.

* * * * *